(12) United States Patent
Robb et al.

(10) Patent No.: US 9,301,463 B1
(45) Date of Patent: Apr. 5, 2016

(54) MULTI-BRACTED LAVENDER PLANTS

(71) Applicant: THE PARADISE SEED COMPANY, PTY LIMITED, Kulnura (AU)

(72) Inventors: John B. Robb, Kariong (AU); Robert J. Cherry, Kulnura (AU)

(73) Assignee: The Paradise Seed Company, PTY Limited, Kulnura (AU)

( * ) Notice: Subject to any disclaimer, the term of this patent is extended or adjusted under 35 U.S.C. 154(b) by 0 days.

(21) Appl. No.: 14/591,229

(22) Filed: Jan. 7, 2015

(51) Int. Cl.
| | | |
|---|---|---|
| *A01H 1/00* | (2006.01) | |
| *A01H 5/02* | (2006.01) | |
| *A01H 1/02* | (2006.01) | |
| *A01H 1/08* | (2006.01) | |
| *C12N 15/82* | (2006.01) | |

(52) U.S. Cl.
CPC .. *A01H 5/02* (2013.01); *A01H 1/02* (2013.01); *A01H 1/08* (2013.01); *C12N 15/827* (2013.01)

(58) Field of Classification Search
USPC .......................................................... Plt./445
See application file for complete search history.

(56) References Cited

PUBLICATIONS

Downderry Nursery, Tender lavender, Jul. 2015.*
Lavender: The genus Lavandula, Chaper 2 by author Tim Upson, Taylor & Francis e-Library 2004 edited by Marina Lis-Balchin.*
Adal et al 2015, Planta 241: 987-1004.*
Upson, T. and Andrews, S. The Genus Lavandula, Jun. 2004, pp. 89-90, 98, and 114-115, Timber Press, Portland Oregon.

* cited by examiner

*Primary Examiner* — David H Kruse
(74) *Attorney, Agent, or Firm* — Bethany R. Roahrig; James M. Weatherly; Cochran Freund & Young, LLC

(57) ABSTRACT

*Lavandula* plants in section *Stoechas* having at least two branched cymeous spikes are disclosed. The present invention further relates to methods for producing *Lavandula* section *Stoechas* plants having branched cymeous spikes, and methods of breeding *Lavandula* plants having branched cymeous spikes, wherein at least one parent plant is a *Lavandula* section *Stoechas* plant having branched cymeous spikes. *Lavandula* section *Stoechas* plants produced by the described methods and characterized by their unique branched cymeous spikes are also described.

25 Claims, 11 Drawing Sheets

FIGURE 1A

*100 simple cymeous spike of a Lavandula section Stoechas plant*

- 107 sterile bracts
- bicincinnus cymes 103
- subtending bract 105
- 101 peduncle
- 109 flower

FIGURE 1B

*Simple cymeous spike from a 6 month old L. stoechas plant*

- 107 sterile bracts
- 111 flower
- Bicincinnus cymes 103
- subtending bract 105
- peduncle 101

FIGURE 1C

*Simple cymeous spike from a 6 month old L. pedunculata plant*

FIGURE 2A 200 branched cymeous spike of the present disclosure 103 bicincinnus cymes sterile bracts 107 lateral spike 201 sterile bracts 203 peduncle 101

109 flowers

195 subtending bract

201

103

FIGURE 2B branched cymeous spike from a 6 month old L. stoechas plant 201 lateral spike sterile bracts 203

FIGURE 2C branched cymeous spike from a 6 month old L. pedunculata plant sterile bracts 107

201 lateral spike sterile bracts 203 peduncle 101

Flow diagram of a breeding scheme that can be used to introduce the phenotype into L. pedunculata

*FIGURE 4B*

*L. pedunculata plant with branched cymeous spikes produced by the breeding scheme shown in Figure 4A*

FIGURE 5A

Flow diagram of a breeding scheme that can be used to introduce the phenotype into L. pedunculata

FIGURE 5B

*L. pedunculata plant with branched cymeous spikes produced by the breeding scheme shown in Figure 5A*

FIGURE 6B

*L. pedunculata plant with branched cymeous spikes produced by the breeding scheme shown in Figure 6A*

FIGURE 7A

*Flow diagram of a breeding scheme that can be used to introduce the phenotype into L. viridis*

Initial cross of *L. stoechas* to *L. viridis*

↓

$F_1$ crossed with *L. stoechas* x *L. pedunculata* hybrid exhibiting branched cymeous spikes

↓

$F_2$ self-pollination

↓

$F_3$ *L. viridis* plant with branched cymeous spikes

*FIGURE 7B*

*L. viridis plant with branched cymeous spikes produced by the breeding scheme shown in Figure 7A*

MULTI-BRACTED LAVENDER PLANTS

BACKGROUND

Lavender is a flowering plant native to Africa, Europe, and Asia, and is cultivated in temperate climates for gardens and landscaping. The flowers may be varying shades of blue, purple, pink, yellow, and white.

A member of the mint family, Lamiaceae, the genus *Lavandula* comprises 40 species of annuals, perennials, evergreen shrubs, and herbs. This genus is categorized into three subgenera: subgenus *Lavandula*, subgenus *Fabricia*, and subgenus *Sabaudia*. The subgenera of *Lavandula* is further subcategorized into three sections: section *Lavandula*, section *Dentatae*, and section *Stoechas*. Species within section *Stoechas* may also be called French lavender, Italian lavender or Spanish lavender.

Section *Stoechas* has three species: *L. stoechas*, *L. pedunculata*, and *L. viridis*. Additionally, there are subspecies of *L. stoechas* and *L. pedunculata*, including subsp. *stoechas*, subsp. *luisieri*, subsp. *pedunculata*, subsp. *cariensis*, subsp. *atlantica*, subsp. *lusitanica*, and subsp. *sampaiana*.

The foregoing examples of related art and limitations related therewith are intended to be illustrative and not exclusive, and they do not imply any limitations on the inventions described herein. Other limitations of the related art will become apparent to those skilled in the art upon a reading of the specification and a study of the drawings.

BRIEF DESCRIPTION OF THE FIGURES

The accompanying figures, which are incorporated herein and form a part of the specification, illustrate some, but not the only or exclusive, example embodiments and/or features. It is intended that the embodiments and figures disclosed herein are to be considered illustrative rather than limiting.

DETAILED DESCRIPTION

Embodiments of the present disclosure may include *Lavandula* plants in section *Stoechas* having at least two branched cymeous spikes. Embodiments of the present disclosure may further comprise *Lavandula* plants in section *Stoechas* having branched cymeous spikes comprising between 15% and 100% of the total inflorescences of the plant as well as lateral spikes having one or more sterile bracts.

In a further embodiment of the present disclosure one or more methods for producing a *Lavandula* plant having branched cymeous spikes are provided. These methods may include, but are not limited to, crossing two *Lavandula* parent plants and harvesting the resultant seed, wherein at least one parent plant is a *Lavandula* section *Stoechas* plant having at least two branched cymeous spikes.

As used herein, the term "branched cymeous spike" refers to an inflorescence as having a primary axis, also known as the peduncle, with smaller lateral spikes arranged radially where one or more sterile bracts are produced at the terminus of each or most of the lateral spikes along with the apex of the peduncle. Each lateral spike has multiple bicincinnus cymes, usually having three to nine flowers each.

*Lavandula* plants in section *Stoechas* normally have an inflorescence that is commonly referred to as a simple spike. A simple spike consists of stalkless flowers arranged along an elongated, unbranched primary axis, the peduncle. This type of simple spike is also described as a cymeous spike, as flowers along the main axis are arranged in small clusters called cymes. Furthermore, *Lavandula* plants in section *Stoechas* are also characterized by large and colored sterile bracts borne at the apex of the spike which has a characteristic bunny ear appearance.

Figure 1A:
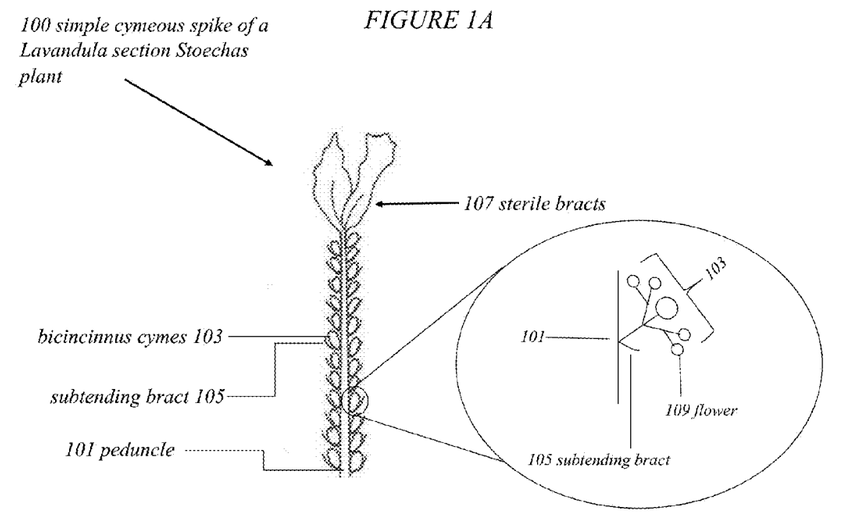
FIG. 1A is an illustration of an example simple cymeous spike of a *Lavandula* section *Stoechas* plant.
Figures 1B, 1C:
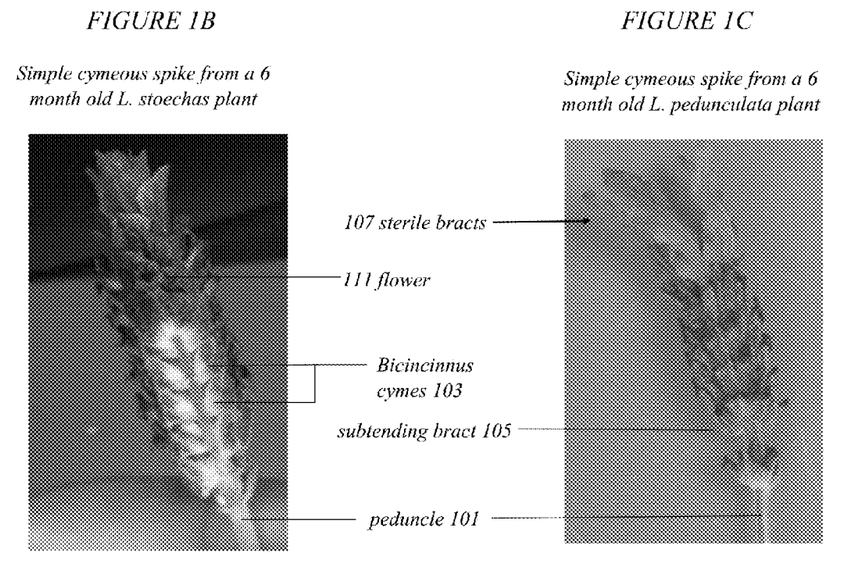
FIG. 1B is a photograph of a simple cymeous spike from 6 month old *Lavandula stoechas*. Some cymes have been removed to show the primary axis, the peduncle.
FIG. 1C is a photograph of a simple cymeous spike from 6 month old *Lavandula pedunculata*. Note the showy sterile bracts at the apex of the primary spike only.

In FIG. 1A, a simple cymeous spike 100 is shown. As shown in FIG. 1A, FIG. 1B and FIG. 1C, a simple cymeous spike consists of stalkless flowers 109 arranged along an elongated, unbranched primary axis of the stalk of the inflorescence, known as the peduncle 101. This type of simple spike is also described as a cymeous spike, as the flowers 109 along the peduncle 101 are arranged in small clusters called bicincinnus cymes 103. As used herein, "bicincinnus cyme" 103 refers to a branching cyme having flowers 109 with a subtending bract 105 located at the base of each bicincinnus cyme 103. The subtending bracts 105 are leaf-like structures located at the node of the peduncle 101 and the bicincinnus cyme 103.

Furthermore, *Lavandula* plants in section *Stoechas* are also characterized by large, colored sterile bracts 107 borne at the apex of the peduncle 101 which have a characteristic bunny ear appearance. Sterile bracts are modified leaves produced in the inflorescence.

An example of a simple cymeous spike from a 6 month old *Lavandula stoechas* plant is shown in the photograph of FIG. 1B. Some cymes 103 have been removed to show the peduncle 101.

An example of a simple cymeous spike from a 6 month old *Lavandula pedunculata* plant having four sterile bracts is shown in FIG. 1C.

As will be discussed in further detail below and in relation to FIG. 1A, branched cymeous spikes are inflorescences that are differentiated from simple cymeous spikes due to the production of lateral spikes branching radially from the peduncle. The branched cymeous spike phenotype of the plants of the present disclosure has been shown through multiple generations of production to be stable and reproduce the branched cymeous spike phenotype. In an embodiment, *Lavandula* plants of the section *Stoechas* of the present disclosure produce inflorescences exhibiting the branched cymeous spike phenotype, an example range of inflorescences exhibiting the branched cymeous spike phenotype may range from 15% to 100% of the total inflorescences of the plant, with one or more sterile bracts at the terminus of each lateral spike, with a range of one to six sterile bracts per lateral spike.

The branched cymeous spike phenotype was discovered in 2000 as a branch mutation through a breeding program conducted by the inventor in Kulnura Australia. Cuttings of the branch mutation were taken and propagated vegetatively. Multiple generations exhibiting the branched cymeous spike were produced and a single clone of *L. stoechas*, exhibiting multiple branched cymeous spikes, was identified in 2005 and designated P2005. P2005 was shown to consistently produce branched cymeous spike inflorescences and has since been clonally propagated. Seed has been produced from several lines derived from line P2005 and plants produced from these crosses have been shown to reproduce the branched cymeous spike phenotype.

Figure 2A:
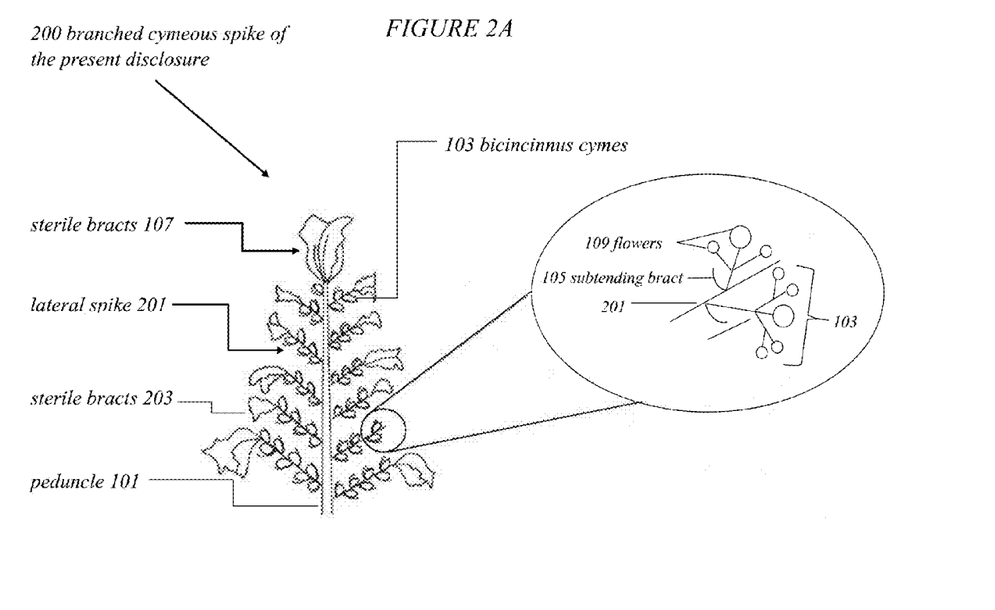
FIG. 2A is an illustration of an example branched cymeous spike and bicincinnus cyme of the present disclosure.
Figures 2B, 2C:
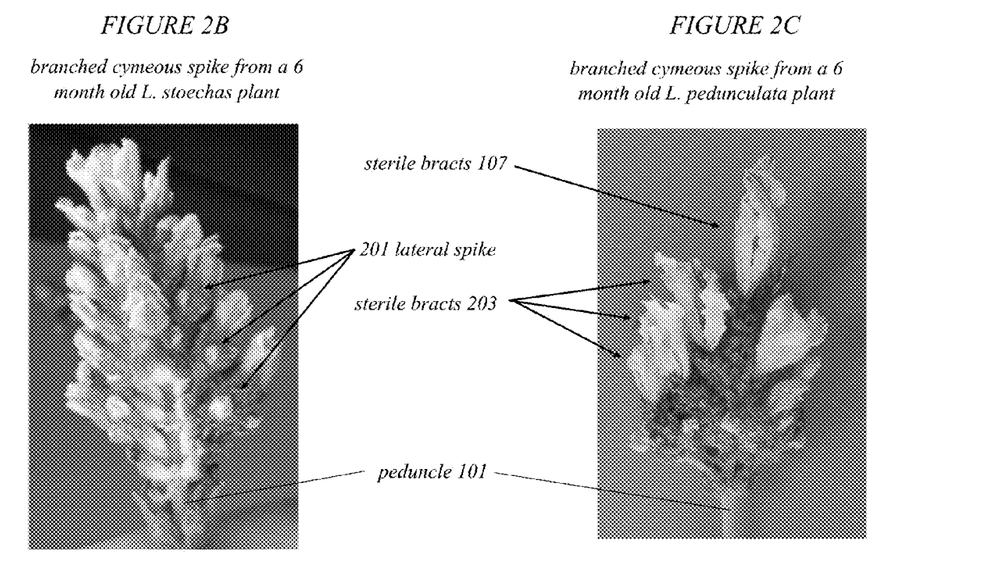
FIG. 2B is a photograph of the new branched cymeous spike from 6 month old *Lavandula stoechas*. Some lateral spikes have been removed to show the primary axis, the peduncle.
FIG. 2C is a photograph of the new branched cymeous spike from 6 month old *Lavandula pedunculata*. Note the showy sterile bracts at the apex of both primary and lateral spikes.

As shown in FIG. 2A, a branched cymeous spike 200 is provided. As discussed previously, an embodiment of the present disclosure relates to *Lavandula* plants in section *Stoechas* having branched cymeous spikes 200. As shown in FIG. 2A, FIG. 2B and FIG. 2C, a branched cymeous spike 200 is an inflorescence that is differentiated from a simple cymeous spike by having lateral spikes 201 arranged radially along the peduncle 101 (the primary axis) with sterile bracts 203 produced at the terminus of each lateral spike 201 in addition to the sterile bracts 107 produced at the apex of the peduncle 101.

As shown in FIG. 2A and FIG. 2C, at the apex of the peduncle 101 and each lateral spike 201 are terminal sterile bracts 107, 203 (please note, sterile bracts 203 are not shown on the lateral spike 201 in expanded view of FIG. 2A). In FIGS. 2A and 2C, two sterile bracts 107 are illustrated at the apex of the peduncle 101, but any number of sterile bracts, with a range of one to six, may be present. Therefore, while this example has two sterile bracts 107, it should be understood that this description is applicable to any *Lavandula* plant in section *Stoechas* having sterile bracts. As with the apex of the peduncle 101, each lateral spike 201 will generally contain at least one sterile bract 203.

Each lateral spike 201 has multiple bicincinnus cymes 103 generally having three to nine flowers 109 each. In the example expanded view of FIG. 2A, two bicincinnus cymes 103 are shown having three and five flowers 109, but any number, usually between three and nine may be present. Therefore, while this descriptive example has bicincinnus cymes 103 having three and five flowers 109, it should be understood that this description is applicable to any bicincinnus cyme 103 of a *Lavandula* section *Stoechas* plant. The subtending bracts 105, when present in branched cymeous spikes, are located at the node of the lateral spike 201 and the bicincinnus cyme 103.

As shown in FIG. 2B, an example of a branched cymeous spike from a 6 month old *Lavandula stoechas* plant is provided. Please note that some lateral spikes 201 have been removed to show the peduncle 101.

Another example of a branched cymeous spike from a 6 month old *Lavandula pedunculata* plant is shown in FIG. 2C.

In Tables 1-4, the plants of the disclosure are compared to commercial varieties 'Bee Brilliant', 'Pukehou' and 'Lavender Lace'. Data was taken from 20 plants, aged 6 months old. Inflorescences were measured when fully mature but did not include any sterile bract discoloration. Weight of average inflorescence does not include the peduncle below the inflorescence. The abbreviation SD refers to the standard deviation. Significance values were obtained using a two-tail P test of equal variance for Table 2, and a two-tail P test of unequal variance for Table 3 and Table 4.

Figure 3:
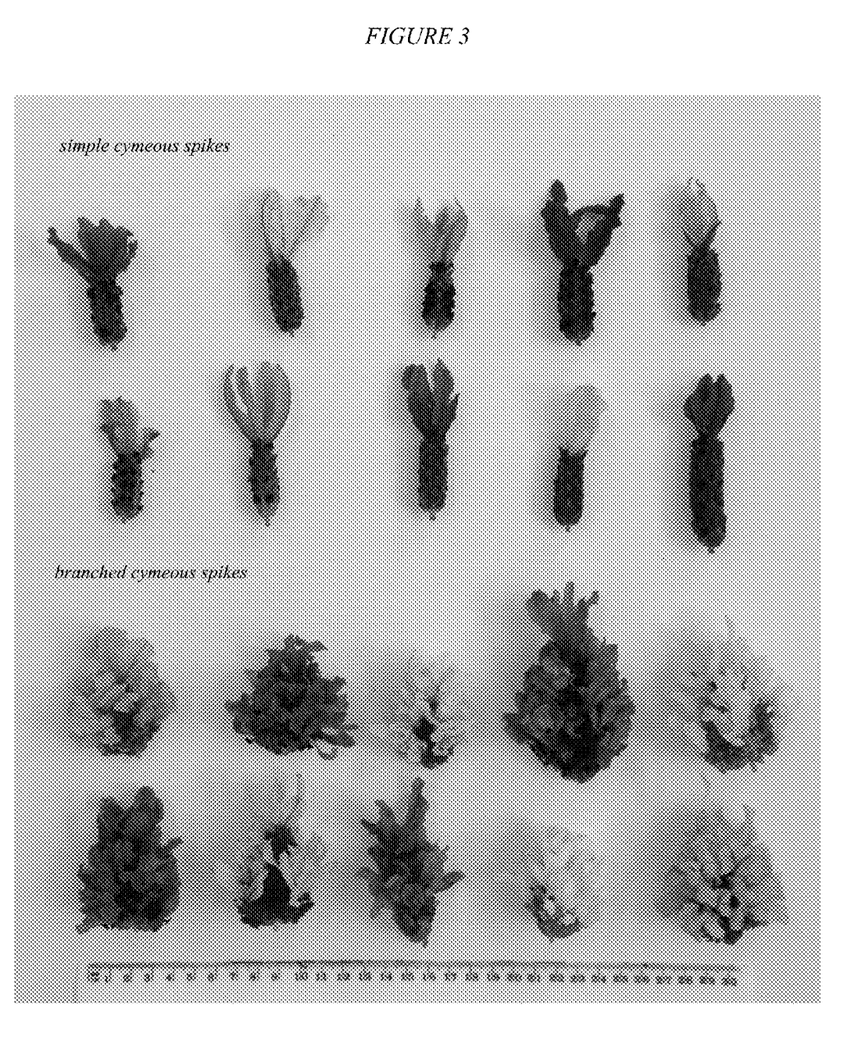
FIG. 3 is a photograph of inflorescences of simple spikes compared to the branched cymeous spikes of the present disclosure.

As shown in FIG. 3 and Table 1, the plants of the present disclosure have much larger inflorescences due to the presence of multiple lateral spikes. While simple cymeous spikes do not exhibit any branching, the plants of the present disclosure have an average number of 17.8 lateral spikes per inflorescence, with a range of 4 to 29. However, a range of 1 to 60 lateral spikes per inflorescence and all integers in between may be present.

TABLE 1

| Number of Lateral Spikes | | |
|---|---|---|
| | Standard Simple Spike | Branched Cymeous Spikes |
| | 0 | 21 |
| | 0 | 29 |
| | 0 | 19 |
| | 0 | 19 |
| | 0 | 20 |
| | 0 | 18 |
| | 0 | 16 |
| | 0 | 15 |
| | 0 | 17 |
| | 0 | 4 |
| SD | 0 | 6.20 |
| AVERAGE | 0 | 17.8 |

As shown in Table 2, the plants of the present disclosure have inflorescences that are approximately double the width of standard simple spike, with average width of 56.8 mm compared to 29.1 mm, which equates to an average 95% increase. Plants of the present disclosure exhibit inflorescences ranging in width from 42 mm to 70 mm and all integers in between, but a wider range of values may be present.

TABLE 2

| Individual Inflorescence Width (mm) | | |
|---|---|---|
| | Standard Simple Spike | Branched Cymeous Spikes |
| | 42 | 60 |
| | 35 | 50 |
| | 16 | 56 |
| | 15 | 55 |
| | 30 | 42 |
| | 35 | 70 |
| | 36 | 70 |
| | 31 | 60 |
| | 25 | 55 |
| | 26 | 50 |
| SD | 8.72 | 8.74 |
| AVERAGE | 29.1 | 56.8 |
| % INCREASE | | 95% |
| P(T <= t) TWO-TAIL | | 1.30037E−06 |

As shown in Table 3, inflorescences of the present disclosure also have greater weight. Plants having a branching cymeous spike of the present disclosure have an average inflorescence weight of 4.35 grams, while the average commercial simple spike varieties have an average inflorescence weight of 1.57 grams, which equates to an average 177% increase. Plants of the present disclosure exhibit inflorescences ranging in weight from 2.70 g to 6.23 g and all integers in between, but a wider range of values may be present. The increased width and weight of the plants of the disclosure is due to the additional lateral spikes, which carry their own bicincinnus cymes, subtending bracts and sterile bracts. The plants of the disclosure also produce more flowers than *Lavandula* plants in section *Stoechas* having simple cymeous spikes, due to the additional bicincinnus cymes present on the lateral spikes (data not shown).

TABLE 3

Individual Inflorescence Weight(g)

|  | Standard Simple Spike | Branched Cymeous Spikes |
|---|---|---|
|  | 1.89 | 4.26 |
|  | 1.51 | 3.48 |
|  | 1.71 | 3.33 |
|  | 2.80 | 6.23 |
|  | 0.98 | 6.08 |
|  | 1.80 | 2.70 |
|  | 1.27 | 6.03 |
|  | 0.92 | 3.58 |
|  | 1.73 | 3.49 |
|  | 1.10 | 4.33 |
| SD | 0.56 | 1.30 |
| AVERAGE | 1.57 | 4.35 |
| % INCREASE |  | 177% |
| P(T <= t) TWO-TAIL |  | 4.486E−05 |

As shown Table 4, plants exhibiting a branching cymeous spike have a 1,062% increase in sterile bracts per inflorescence, since each lateral spike, in addition to the primary spike, carry their own set of showy sterile bracts. Plants of the disclosure have inflorescences with an average of 60.4 sterile terminal bracts compared to an average of 5.2 sterile terminal bracts for simple spikes. Plants of the disclosure exhibit a range of 23 to 70 sterile bracts per inflorescence, but a range of 2 to 300 and all integers in between may be present.

TABLE 4

Number of Sterile Terminal Bracts per Inflorescence

|  | Standard Simple Spike | Branched Cymeous Spikes |
|---|---|---|
|  | 4 | 70 |
|  | 4 | 72 |
|  | 6 | 65 |
|  | 7 | 76 |
|  | 6 | 75 |
|  | 5 | 68 |
|  | 4 | 50 |
|  | 6 | 45 |
|  | 4 | 60 |
|  | 6 | 23 |
| SD | 1.14 | 16.69 |
| AVERAGE | 5.2 | 60.4 |
| % INCREASE |  | 1,062% |
| P(T <= t) TWO-TAIL |  | 2.50572E−06 |

Embodiments of the present disclosure may also include a *Lavandula* section *Stoechas* inflorescence exhibiting a branching cymeous spike with between 1 and 60 lateral spikes.

Embodiments of the present disclosure further include a *Lavandula* section *Stoechas* inflorescence exhibiting a branching cymeous spike having a weight of between 2.5 grams and 6.5 grams.

Embodiments of the present disclosure further include a *Lavandula* section *Stoechas* inflorescence exhibiting a branching cymeous spike and having between 2 and 300 sterile terminal bracts.

Embodiments of the present disclosure further include a plant part, wherein said plant part comprises a cell, seed, protoplast, tissue culture, or vegetative cutting produced from *Lavandula* section *Stoechas* plants having branched cymeous spikes, and plants regenerated therefrom.

Embodiments of the present disclosure further include methods for producing *Lavandula* plants having at least two branched cymeous spikes. An example method may include crossing two *Lavandula* parent plants and harvesting the resultant seed, wherein at least one *Lavandula* parent plant is a *Lavandula* section *Stoechas* plant having branched cymeous spikes.

An additional method for producing *Lavandula* plants having branched cymeous spikes may include, but is not limited to, intraspecific hand hybridization. Using a *Lavandula* section *Stoechas* plant having branched cymeous spikes as a male or female parent, an initial cross is performed with a normal flowering *Lavandula* plant within section *Stoechas* or with a hybrid of section *Stoechas*. The resulting seeds are sown and the seedlings are grown according to conventional methods. The flowering $F_1$ progeny are then scored for branched cymeous spikes and those selected may be further crossbred with siblings or half siblings, or backcrossed to the branched cymeous spiked parent, or self-pollinated, or outcrossed to another species. Additional crosses may be performed, and subsequent progeny ($F_2$, $F_3$, $F_4$, etc.) may be further crossbred with siblings or half siblings, or backcrossed to the branched cymeous spiked parent, or self-pollinated, or outcrossed to another species. Chosen plants having branched cymeous spikes may then be clonally propagated to ensure stability of the trait.

As will be understood by one skilled in the art once they understand the scope of the embodiments, additional breeding methods may be used to produce *Lavandula* plants having at least two branched cymeous spikes as described herein. Example methods may also include, sib- and half-sib crossing, backcrossing, and outcrossing with other *Lavandula* section *Stoechas* to increase genetic diversity and, incorporate desirable traits, as well as prevent inbreeding depression.

The branched cymeous spike phenotype can be predictably bred into other *Lavandula* section *Stoechas* plants having different genetic backgrounds using the methods described hereinabove. *Lavandula* section *Stoechas* cultivars having the branched cymeous spike phenotype can be predictably selected in which the plants exhibit branched spikes comprising 15% to 100% of the total inflorescences and/or have an increased inflorescence size and weight. The degree of percentage of inflorescences, inflorescence biomass or inflorescence size can be predictably increased by means of recurrent selection. The branched cymeous spike phenotype can be predictably combined with other desirable *Lavandula* characteristics to produce commercially acceptable cultivars that can be stably reproduced by asexual propagation.

Embodiments of the present disclosure further include seeds, plants, and plant parts produced from crossing two *Lavandula* parent plants, wherein at least one parent plant is a *Lavandula* section *Stoechas* plant having at least two branched cymeous spikes.

Embodiments of the present disclosure include a *Lavandula* section *Stoechas* plant having branched cymeous spikes, wherein a representative sample of seed of said plant has been deposited under NCIMB Accession No. 42347.

Embodiments of the present disclosure further include seeds, plants, and plant parts produced from *Lavandula* section *Stoechas* plants having branched cymeous spikes, wherein a representative sample of seed of said *Lavandula* section *Stoechas* plant has been deposited under NCIMB Accession No. 42347.

As shown in Table 5, the genus *Lavandula* is divided into three subgenera, *Lavandula, Fabricia, and Sabaudia*. The subgenus *Lavandula* is divided into three Sections: section *Lavandula*, section *Dentatae*, and section *Stoechas*. Section *Stoechas* has three species: *L. stoechas, L. pedunculata*, and *L. viridis*. Additionally, there are subspecies of *L. stoechas* and *L. pedunculata*, including subsp. *stoechas*, subsp. *luisieri*, subsp. *pedunculata*, subsp. *cariensis*, subsp. *atlantica*, subsp. *lusitanica*, and subsp. *sampaiana*.

TABLE 5

Genus *Lavandula* taxonomy

| Subgenus | Section | Species | Subspecies |
|---|---|---|---|
| Lavandula | Stoechas | L. stoechas | subsp. stoechas |
| | | | subsp. luisieri |
| | | L. pedunculate | subsp. pedunculata |
| | | | subsp. cariensis |
| | | | subsp. atlantica |
| | | | subsp. lusitanica |
| | | | subsp. sampaiana |
| | | L. viridis | none |
| | Lavandula | L. angustifolia | subsp. angustifolia |
| | | | subsp. pyrenaica |
| | | L. latifolia | none |
| | | L. lanata | none |
| | Dentatae | L. dentata | 2 varieties |
| Fabricia | Pterostoechas | L. multifida | none |
| | | L. canariensis | 7 subspecies* |
| | | L. minutolii | 2 varieties |
| | | L. bramwellii | none |
| | | L. pinnata | none |
| | | L. buchii | 3 varieties |
| | | L. rotundifolia | none |
| | | L. maroccana | none |
| | | L. tenuisecta | none |
| | | L. rejdalii | none |
| | | L. mairei | 2 varieties |
| | | L. coronopifolia | none |
| | | L. saharica | none |
| | | L. antineae | subsp. antinae |
| | | | subsp. marrana |
| | | | subsp. tibestica |
| | | L. pubescens | none |
| | | L. citriodora | none |
| | Subnudae | L. subnuda | none |
| | | L. macra | none |
| | | L. dhofarensis | subsp. dhofarensis |
| | | | subsp. ayunensis |
| | | L. samhanensis | none |
| | | L. setifera | none |
| | | L. qishnensis | none |
| | | L. nimmoi | none |
| | | L. galgalloensis | none |
| | | L. aristibracteata | none |
| | | L. somaliensis | none |
| | Chaetostachys | L. bipinnata | none |
| | | L. gibsonii | none |
| | Hasikenses | L. hasikensis | none |
| | | L. sublepiodota | none |
| Sabaudia | Sabaudia | L. atriplicifolia | none |
| | | L. erythraeae | none |

*7 subspecies of *L. canariensis* include subsp. *canariensis*, subsp. *gomerensis* subsp. *palmensis*, subsp. *hierrensis*, subsp. *lancerottensis*, and subsp. *fuerteventurae*.

The subgenus *Fabricia* is divided into four Sections: section *pterostoechas*, section *Subnudae*, section *Chaetostachys*, and section *Hasikenses*. Each section of *Fabricia* is further divided into species and occasionally, subspecies. Subgenus *Sabaudia* has one section, *Sabaudia*, which is divided into two species: *L. atriplicifolia* and *L. erythraeae*.

Embodiments of the present disclosure further include methods for producing interspecific seeds, plants, and plant parts by from crossing two *Lavandula* section *Stoechas* plants, wherein at least one plant is a *Lavandula* section *Stoechas* plant having branched cymeous spikes and the other is selected from the group consisting of *Lavandula pedunculata* or *Lavandula viridis*.

Embodiments of the present disclosure further include *Lavandula* section *Stoechas* interspecific hybrids having branched cymeous spikes, wherein said branched cymeous spikes comprise 15% to 100% of the total inflorescences on said hybrid plant, and wherein said inflorescences have between 1 and 60 lateral spikes.

Embodiments of the present disclosure further include seeds, plants, and plant parts produced from crossing two *Lavandula* section *Stoechas* plants, wherein at least one *Lavandula* plant is a *Lavandula* section *Stoechas* plant having at least two branched cymeous spikes and the other is selected from the group consisting of subsp. *stoechas*, subsp. *luisieri*, subsp. *pedunculata*, subsp. *cariensis*, subsp. *atlantica*, subsp. *lusitanica*, or subsp. *sampaiana*.

Embodiments of the present disclosure further include methods for producing intersectional hybrids having branched cymeous spikes by altering the chromosome number of *Lavandula* section *Stoechas* plants having branched cymeous spikes, such that they are then favorable to crosses with other lavender plants, including those within section *Lavandula* and section *Dentatae*. As used herein, intersectional hybrid refers to a plant produced by crossing two *Lavandula* plants from different sections.

Embodiments of the present disclosure further include intersubgeneric hybrids having branched cymeous spikes that may be produced by altering the chromosome number of *Lavandula* section *Stoechas* plants having branched cymeous spikes, such that they are then favorable to crosses with other lavender plants, including those within the subgenus *Fabricia* and the subgenus *Sabaudia*. As used herein, intersubgeneric hybrid refers to plants produced by crossing two *Lavandula* plants from different subgenera.

EXAMPLES

The following examples are provided to illustrate further the various applications and are not intended to limit the invention beyond the limitations set forth in the appended claims.

Example 1

The Phenotype of Plants of the Present Disclosure

The branched cymeous spike phenotype described herein can be altered via standard growing techniques and environments to include inflorescences having only 1 lateral spike, so as to appear as a double spike, as well as those having up to 60 lateral spikes on a single inflorescence. Such inflorescences may have between 2 and 300 sterile bracts per inflorescence.

Example 2

Incorporating the Phenotype into Additional *L. stoechas* Lines

The branched cymeous spike phenotype as described herein can be bred into other *L. stoechas* lines having other flower colors and desirable characteristics. Crosses can be performed over several generations, and may include sib and half-sib crossing, backcrossing, and self-pollination. Plants may also be generated by protoplast fusion, a technique well known in the art. Plants can be selected for the branched cymeous spike phenotype as well as other desirable characteristics, including, but not limited to, flower color, oil content, drought tolerance, disease resistance, and pest resistance.

Example 3

Incorporating the Branched Cymeous Spike Phenotype into *L. pedunculata*

Figure 4A:
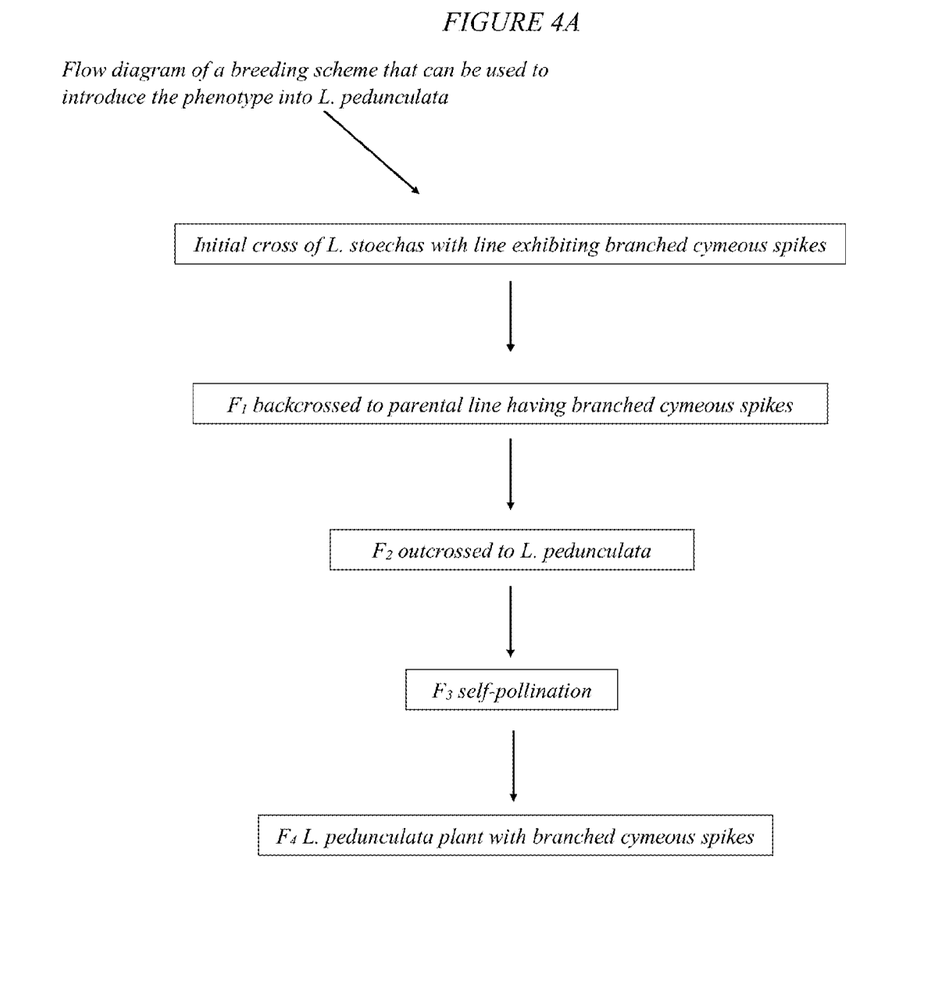
FIG. 4A is a flow diagram of a breeding scheme that can be used to introduce the phenotype into *L. pedunculata*.

As shown in FIG. 4A, the phenotype of the present disclosure was introduced into *L. pedunculata* through conventional breeding techniques. As outlined in flow diagram, a plant having branched cymeous spikes, P2005, was crossed with a proprietary line of *L. stoechas*, B01-12. The $F_1$ progeny (SP 3385) was then backcrossed to the parental line having branched cymeous spikes, P2005. The $F_2$ progeny, designated 3P, was outcrossed to a proprietary line of *L. pedunculata* designated 1038. The resultant $F_3$ progeny was allowed to self-pollinate to produce an $F_4$ progeny *L. pedunculata* plant with branched cymeous spikes that is stable and reproduces true to type.

Figure 4B:
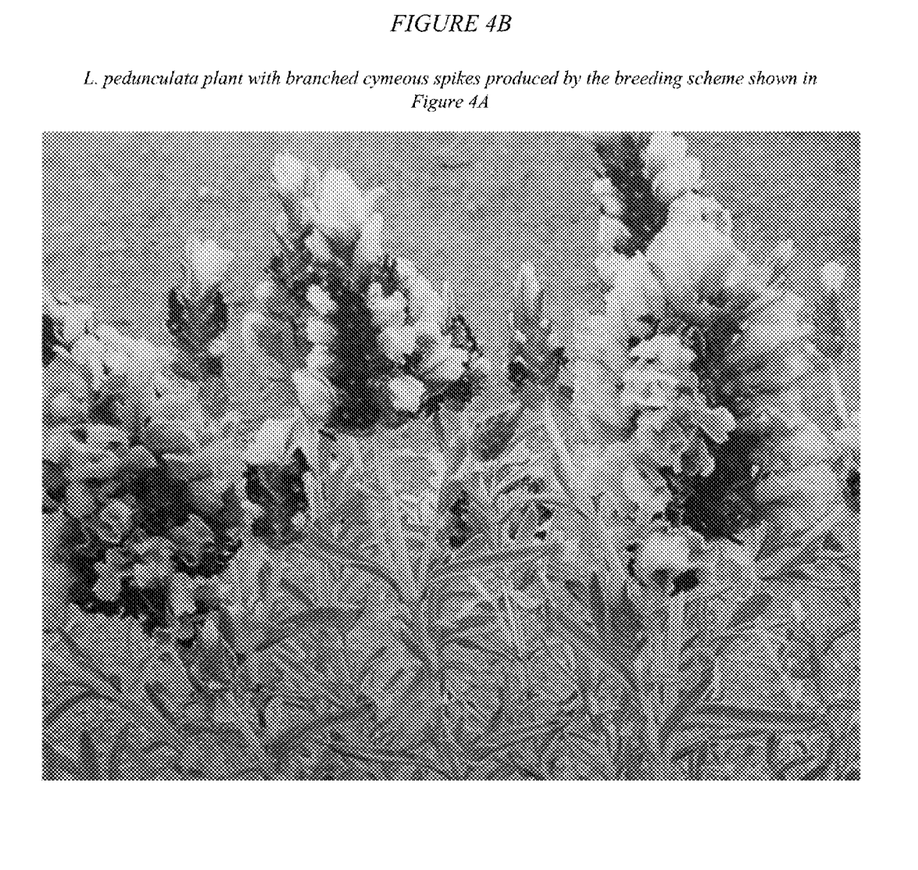
FIG. 4B is a photograph of a *L. pedunculata* plant with branched cymeous spikes produced by the breeding scheme shown in FIG. 4A.

Not shown in FIG. 4A but shown in FIG. 4B is a *L. pedunculata* plant having branched cymeous spikes produced using the flow diagram outlined in FIG. 4A.

Example 4

Incorporating the Branched Cymeous Spike Phenotype into *L. pedunculata*

Figure 5A:
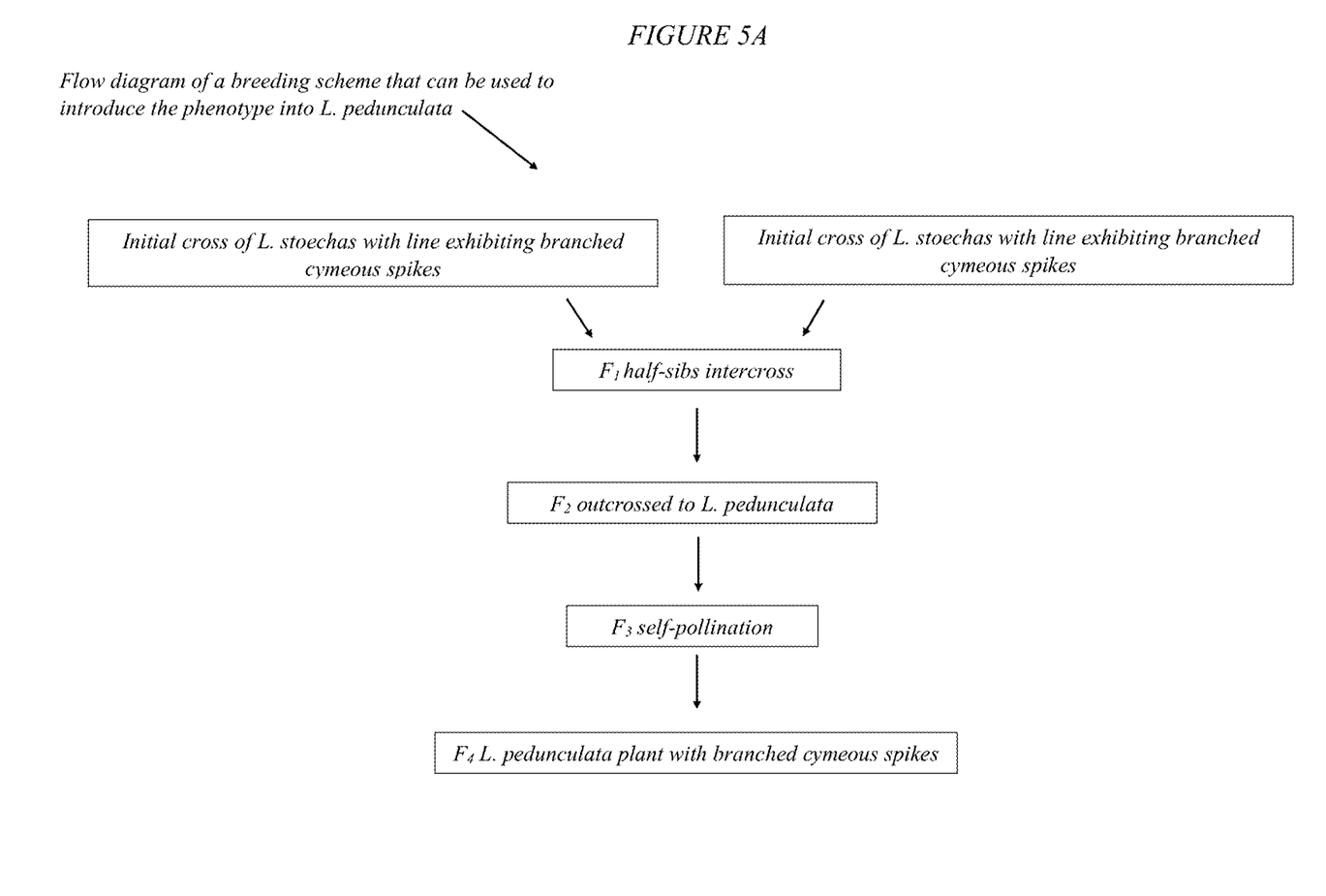
FIG. 5A is a flow diagram of a breeding scheme that can be used to introduce the phenotype into *L. pedunculata*.

As shown in FIG. 5A, the phenotype of the present disclosure was introduced into *L. pedunculata* through conventional breeding techniques. As outlined in the flow diagram, plants exhibiting branched cymeous spikes, P2005, were crossed with two different proprietary lines of *L. stoechas*, designated B01-02 and B01-33. The $F_1$ half-sibs, designated SP 651 and SP 657, were then intercrossed and the resultant $F_2$ progeny, SP 3387, was outcrossed to a proprietary line of *L. pedunculata*, designated 1052. $F_3$ progeny were allowed to self-pollinate to produce an $F_4$ progeny *L. pedunculata* plant with branched cymeous spikes that is stable and reproduces true to type.

Figure 5B:
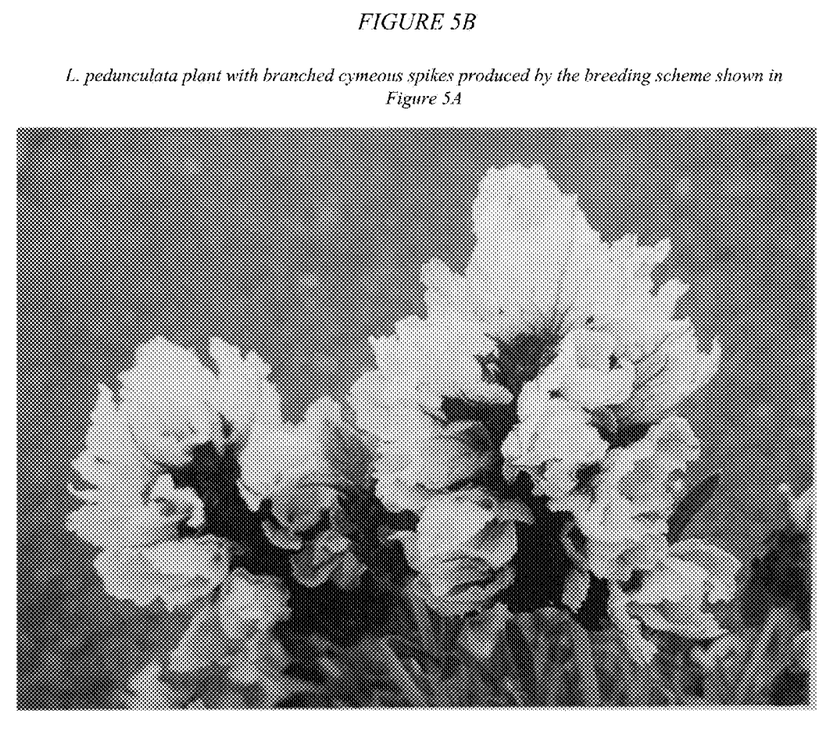
FIG. 5B is a photograph of a *L. pedunculata* plant with branched cymeous spikes produced by the breeding scheme shown in FIG. 5A.

Not shown in FIG. 5A but shown in FIG. 5B is a *L. pedunculata* plant having branched cymeous spikes produced using the flow diagram outlined in FIG. 5A.

Example 5

Incorporating the Branched Cymeous Spike Phenotype into *L. pedunculata*

Figure 6A:
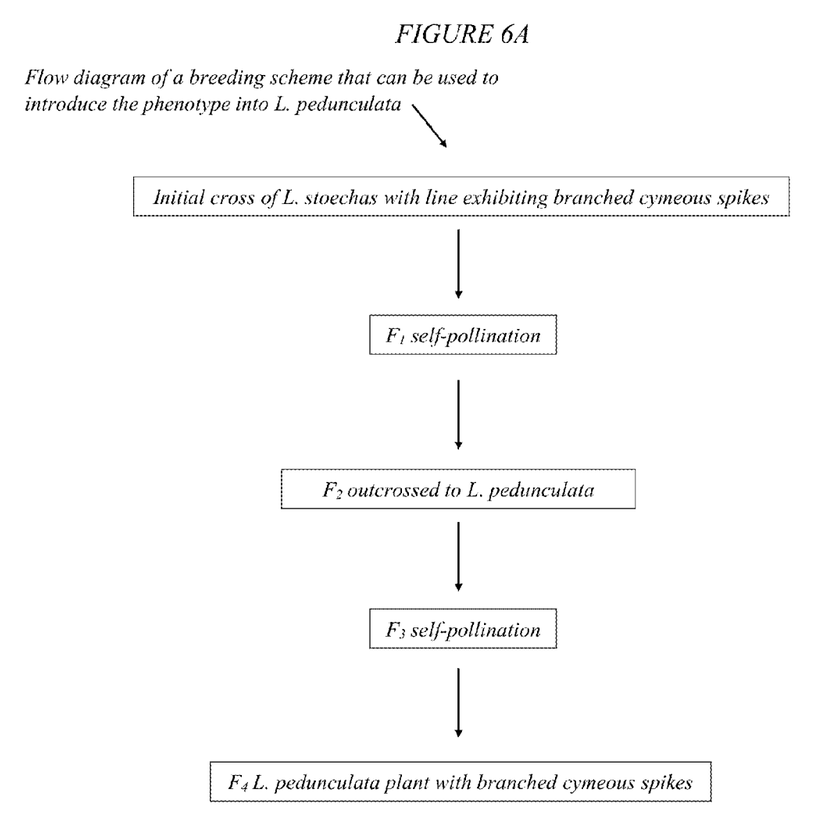
FIG. 6A is a flow diagram of a breeding scheme that can be used to introduce the phenotype into *L. pedunculata*.

As shown in FIG. 6A, the phenotype of the present disclosure was introduced into *L. pedunculata* through conventional breeding techniques. As outlined in the flow diagram, a plant exhibiting branched cymeous spikes, P2005, was crossed with a proprietary line of *L. stoechas*, B01-02. The $F_1$ progeny was allowed to self-pollinate and the $F_2$ progeny, SP 3387, was then outcrossed to a proprietary line of *L. pedunculata*, designated 1052. $F_3$ progeny were allowed to self-pollinate to produce an $F_4$ progeny *L. pedunculata* plant with branched cymeous spikes that is stable and reproduces true to type.

Figure 6B:
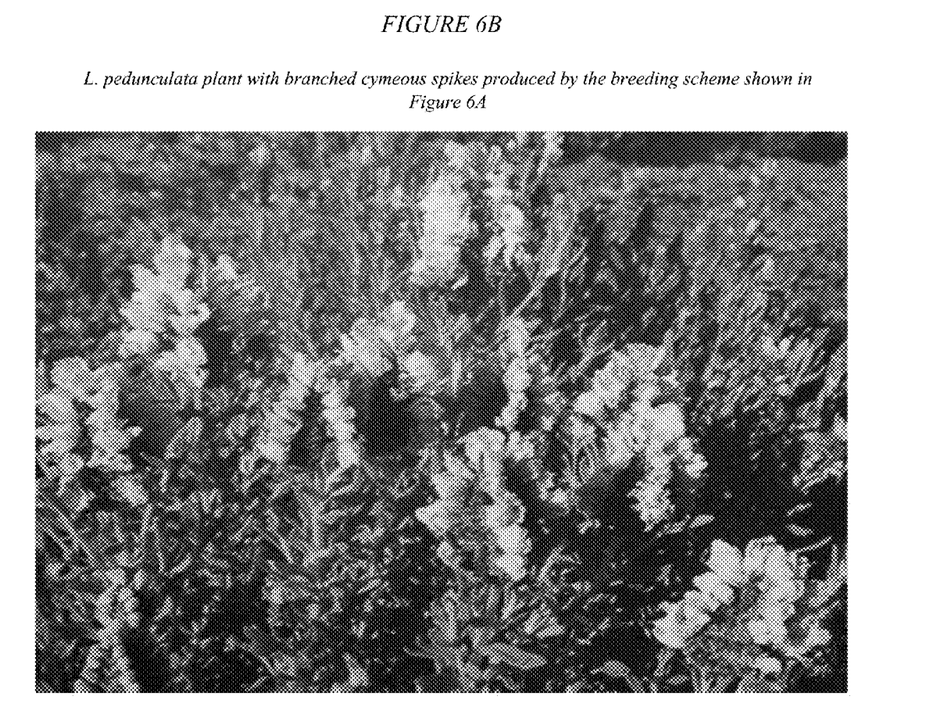
FIG. 6B is a photograph of a *L. pedunculata* plant with branched cymeous spikes produced by the breeding scheme shown in FIG. 6A.

Not shown in FIG. 6A but shown in FIG. 6B is a *L. pedunculata* plant having branched cymeous spikes produced using the flow diagram outlined in FIG. 6A.

Example 6

Incorporating the Branched Cymeous Spike Phenotype into L. *Viridis*

Figure 7A:
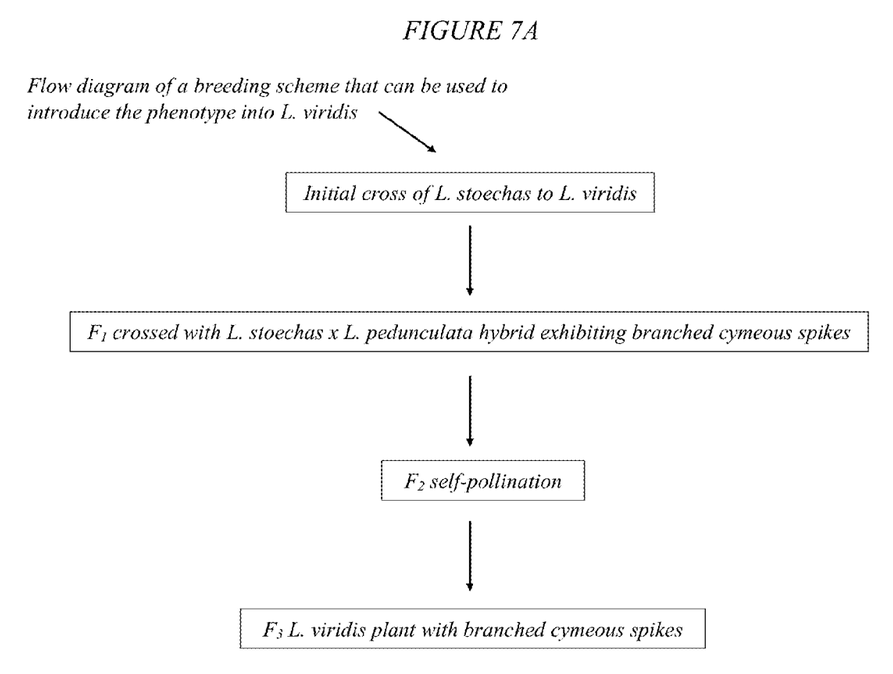
FIG. 7A is a flow diagram of a breeding scheme that can be used to introduce the phenotype into *L. viridis*.

As shown in FIG. 7A, the phenotype of the present disclosure was introduced into *L. viridis* through conventional breeding techniques. As outlined in the flow diagram, a *L. stoechas* plant, designated COCWOB, was crossed with a proprietary line of *L. viridis*. The $F_1$ progeny, designated 1050443, was then crossed to proprietary *L. stoechas*×*L. pedunculata* hybrid line exhibiting branched cymeous spikes, designated SP 1050440. The $F_2$ progeny, designated 1161, was allowed to self-pollinate to produce an $F_3$ progeny *L. viridis* plant with branched cymeous spikes that is stable and reproduces true to type.

Figure 7B:
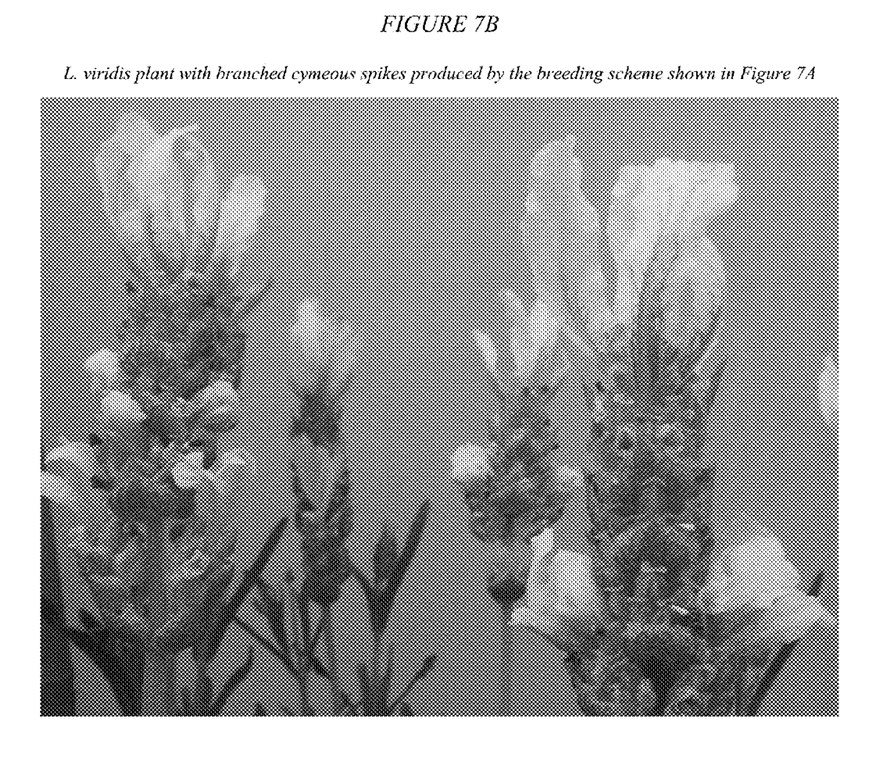
FIG. 7B is a photograph of a *L. viridis* plant with branched cymeous spikes produced by the breeding scheme shown in FIG. 7A.

Not shown in FIG. 7A but shown in FIG. 7B is a *L. viridis* plant having branched cymeous spikes produced using the flow diagram outlined in FIG. 7A.

Example 7

Generating Interspecific Hybrids

The phenotype of the present disclosure can be bred into interspecific hybrids. The subspecies of *L. stoechas*, subsp. *stoechas* and subsp. *luisieri*, may be bred together (*L. stoechas* subsp. *stoechas*×*L. stoechas* subsp. *luisieri*). Subspecies of *L. pedunculata*, including subsp. *pedunculata*, subsp. *cariensis*, subsp. *atlantica*, subsp. *lusitanica*, and subsp. *sampaiana* may be bred together. For example, *L. pedunculata* subsp. *atlantica* may be crossed with *L. pedunculata* subsp. *pedunculata*. Additionally, subspecies of *L. stoechas* and *L. pedunculata* may be bred together. For example, *L.*×*cadevallii* is a hybrid produced from crossing *L. pedunculata* subsp. *pedunculata* and *L. stoechas*, subsp. *stoechas*.

Further still, the subspecies of *L. stoechas* and *L. pedunculata* may be crossed with *L. viridis* (*L. pedunculata* and *L. stoechas*×*L. viridis* hybrids). For example, *L.*×*alportelensis* is a hybrid produced from crossing *L. stoechas* subsp. *luisieri* and *L. viridis*. *L.*×*limae* is a hybrid produced from crossing *L. pedunculata* subsp. *lusitanica* and *L. viridis*.

Example 8

Generating Intersectional Hybrids

In an embodiments of the present disclosure, intersectional hybrids having branched cymeous spikes may be produced by altering the chromosome number of *Lavandula* section *Stoechas* plants having branched cymeous spikes, such that they are then favorable to crosses with other *Lavandula* plants, including those within section *Lavandula* and section *Dentatae*. For example, an intersectional hybrid can be produced from crossing *L. dentata* (from section *Dentatae*) and *L. latifolia* (from section *Lavandula*). Methods of altering plant chromosome number may comprise using anti-miotic agents, which may include but is not limited to, colchicine, trifluralin, oryzalin, and amiprophos-methyl (APM), or may comprise irradiation. Methods of using colchicine or other anti-miotic agents are well known in the art, as discussed in Poehlman, J. M., *Breeding Field Crops*, University of Missouri, Hold, Rinehart and Winston Inc. (1996); Watts, L. *Flower and Vegetable Plant Breeding*, Grower Boods (1980); Callaway D. J. and Callaway M. B., *Breeding Ornamental Plants*, Timber Press Inc. (2000).

Example 9

Generating Intersubgeneric Hybrids

In an embodiments of the present disclosure, intersubgeneric hybrids having branched cymeous spikes may be produced by altering the chromosome number of *Lavandula* section *Stoechas* plants having branched cymeous spikes, such that they are then favorable to crosses with other *Lavandula* plants, including those within the subgenus *Fabricia* and the subgenus *Sabaudia*. Methods of altering plant chromosome number may comprise using anti-miotic agents, which may include but is not limited to, colchicine, trifluralin, oryzalin, and APM, or may comprise irradiation. Methods of using colchicine or other anti-miotic agents are well known in the art, as discussed in Poehlman, J. M., *Breeding Field Crops*, University of Missouri, Hold, Rinehart and Winston Inc. (1996); Watts, L. *Flower and Vegetable Plant Breeding*, Grower Boods (1980); Callaway D. J. and Callaway M. B., *Breeding Ornamental Plants*, Timber Press Inc. (2000).

Example 10

Clonally Propagating *Lavandula* Plants Having Branched Cymeous Spikes

In an embodiment of the present disclosure any *Lavandula* plant having branched cymeous spikes can be asexually propagated. Cuttings for asexual propagation can be taken at any time of the year from plants mature enough to provide cutting material, usually older than 3 months, and no special hormones or soil mixtures are used.

*Lavandula* plants may also be propagated by tissue culture. While a number of protocols exist and can be used to generate *Lavandula* plants by tissue culture, the following protocol may be used. *Lavandula* plants can be initiated in vitro by disinfection using sodium hypochlorite and shoot tips placed in test tubes containing modified Murashige and Skoog media. Clean (bacteria and fungus free) lab mother stock of *Lavandula* can be maintained and produced in vitro using modified Murashige and Skoog media supplemented with cytokinin to promote axillary branching. Cultures can be rooted on modified murashige and Skoog media supplemented with auxin to promote rooting.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

A representative sample of seed of *Lavandula* section *Stoechas*, including *L. stoechas, L. pedunculata, L. viridis,* and subspecies and interspecific hybrids within section *Stoechas*, where plants produced from the representative seed are capable of displaying the branched cymeous spikes phenotype of the present disclosure, has been placed on deposit under the Budapest Treaty with the National Collections of Industrial, Food and Marine Bacteria (NCIMB), Ferguson Building, Craibstone Estate, Bucksburn, Aberdeen, Scotland, AB21 9YA, United Kingdom under NCIMB Accession No. 42347. The date of the deposit was Dec. 23, 2014. All restrictions upon availability to the public will be irrevocably removed upon granting of the patent in accordance with 37 C.F.R. §1.808(a)(2), and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced as necessary during that period.

We claim:

1. A *Lavandula* section *Stoechas* plant comprising the mutation contained in line P2005 that produces a branched cymeous spikes phenotype, wherein a representative sample of seed of said *Lavandula* section *Stoechas* plant containing said mutation that produces said phenotype having been deposited under NCIMB Accession No. 42347.

2. A seed produced from the *Lavandula* section *Stoechas* plant of claim 1.

3. A *Lavandula* section *Stoechas* plant comprising the mutation contained in line P2005 that produces a branched cymeous spike phenotype, wherein said plant is produced from seed deposited under NCIMB Accession No. 42347.

4. A *Lavandula* section *Stoechas* plant produced from the seed of claim 2, wherein between 15% and 100% of the inflorescences of the entire plant are branched cymeous spikes.

5. The *Lavandula* section *Stoechas* plant of claim 1, wherein said plant having said phenotype has branched cymeous spikes that comprise between 15% and 25% of the inflorescences of the entire plant.

6. The *Lavandula* section *Stoechas* plant of claim 1, wherein said plant having said phenotype has branched cymeous spikes that comprise between 26% and 35% of the inflorescences of the entire plant.

7. The *Lavandula* section *Stoechas* plant of claim 1, wherein said plant having said phenotype has branched cymeous spikes that comprise between 36% and 45% of the inflorescences of the entire plant.

8. The *Lavandula* section *Stoechas* plant of claim 1, wherein said plant having said phenotype has branched cymeous spikes that comprise between 46% and 55% of the inflorescences of the entire plant.

9. The *Lavandula* section *Stoechas* plant of claim 1, wherein said plant having said phenotype has branched cymeous spikes that comprise between 56% and 100% of the inflorescences of the entire plant.

10. A plant part produced from the plant of claim 1, wherein said plant part comprises a cell, seed, protoplast, tissue culture, or vegetative cutting.

11. A *Lavandula* section *Stoechas* plant regenerated from the cell, seed, protoplast, tissue culture, or vegetative cutting of claim 10, wherein said plant has said phenotype having at least two branched cymeous spikes.

12. The *Lavandula* section *Stoechas* plant of claim 1, wherein said branched cymeous spike has between 1 and 60 lateral spikes.

13. The *Lavandula* section *Stoechas* plant of claim 1, wherein the average weight of said branched cymeous spike has a weight of between 2.5 grams and 6.5 grams.

14. The *Lavandula* section *Stoechas* plant of claim 1, wherein said branched cymeous spike has between 2 and 300 terminal bracts.

15. The *Lavandula* section *Stoechas* plant of claim 1, wherein said plant having said phenotype is selected from the group consisting of *Lavandula stoechas*, *Lavandula pedunculata*, and *Lavandula viridis*.

16. A method for producing a *Lavandula* plant having a branched cymeous spikes phenotype, wherein the method comprises crossing two *Lavandula* parent plants and harvesting the resultant seed, wherein at least one parent plant is a *Lavandula* section *Stoechas* plant comprising the mutation contained in line P2005 that produces a branched cymeous spike phenotype, wherein said branched cymeous spikes comprise between 15% and 100% of the inflorescences of the entire plant, wherein a representative sample of seed of said *Lavandula* section *Stoechas* plant containing said mutation having been deposited under NCIMB Accession No. 42347, and wherein the second parent plant is selected from the group consisting of *Lavandula stoechas*, *Lavandula pedunculata*, or *Lavandula viridis*.

17. A *Lavandula* seed produced from the method of claim 16.

18. A *Lavandula* plant, or part thereof, having said branched cymeous spikes phenotype produced by growing the seed of claim 17, wherein said plant has branched cymeous spikes that comprise between 15% and 100% of the inflorescences of the entire plant.

19. The method of claim 16, wherein said second parent plant is a subspecies of *Lavandula stoechas*, or *Lavandula pedunculata*, and is selected from the group consisting of subspecies *stoechas*, subspecies *luisieri*, subspecies *pedunculata*, subspecies *cariensis*, subspecies *atlantica*, subspecies *lusitanica*, or subspecies *sampaiana*.

20. The method of claim 16, wherein said parent plants are *Lavandula stoechas* and further comprising:
   backcrossing the $F_1$ progeny to said parent having said branched cymeous spike phenotype and producing an $F_2$ progeny;
   outcrossing the $F_2$ progeny to a *Lavandula* section *Stoechas* plant and producing an $F_3$ progeny;
   self-pollinating the $F_3$ progeny; and
   producing a *Lavandula* section *Stoechas* plant having a branched cymeous spike phenotype having two or more branched cymeous spikes.

21. The method of claim 20, wherein said $F_1$ progeny is self-pollinated.

22. The method of claim 20, wherein said $F_1$ progeny are intercrossed.

23. The method of claim 20, wherein said $F_2$ progeny are outcrossed to *Lavandula pedunculata*.

24. The method of claim 20, wherein said $F_2$ progeny are outcrossed to *Lavandula viridis*.

25. The method of claim 16, wherein an interspecific hybrid having said branched cymeous spike phenotype is produced, wherein said branched cymeous spikes comprise between 15% and 100% of the total inflorescences on said hybrid plant.

* * * * *